United States Patent [19]
Davies et al.

[11] Patent Number: 5,552,600
[45] Date of Patent: Sep. 3, 1996

[54] PRESSURE STABILIZED ION MOBILITY SPECTROMETER

[75] Inventors: John H. Davies; Ronald A. Jackson, both of Mississauga; Frank J. Kuja, Brampton, all of Canada

[73] Assignee: Barringer Research Limited, Rexdale, Canada

[21] Appl. No.: 477,321

[22] Filed: Jun. 7, 1995

[51] Int. Cl.[6] .............................. B01D 59/44; H01J 49/40
[52] U.S. Cl. .......................................... 250/286; 250/289
[58] Field of Search ..................................... 250/286, 287, 250/288, 289

[56] References Cited

U.S. PATENT DOCUMENTS 2,714,164  7/1955  Riggle et al. ........................... 250/289
4,777,363  10/1988  Eiceman et al. ........................ 250/286
5,237,175  8/1993  Wells ..................................... 250/288
5,268,572  12/1993  Mordehai et al. ...................... 250/291

*Primary Examiner*—Bruce C. Anderson

[57] ABSTRACT

The gas pressure in an ion mobility spectrometer is controlled to maintain near-constant pressure in the drift region by adjusting gas flows in response to a pressure transducer output. The pressure in the system may be referenced to ambient pressure. The increase in pressure stability achieved permits the expected drift times of target analytes to be determined much more accurately than otherwise, and thereby allows more specific detection parameters to be used. This in turn results in a significantly improved false alarm rate for the device.

10 Claims, 3 Drawing Sheets

SCHEMATIC OF TYPICAL PRESSURE BEHAVIOUR IN PRIOR ART IMS

SCHEMATIC OF TYPICAL PRESSURE BEHAVIOUR FOR THE PRESSURE STABILIZED IMS

PRESSURE STABILIZED ION MOBILITY SPECTROMETER

FIELD OF THE INVENTION

This invention relates to an ion mobility spectrometry (IMS) instrument that detects chemicals present as vapours in the air or other gases, or liberated as vapours from condensed phases such as particles or solutions. It particularly relates to the detection with a low false alarm rate of explosives, narcotics, and other contraband concealed in belongings, or in transported goods and cargo.

BACKGROUND OF THE INVENTION

Ion mobility spectrometry—IMS—instruments operate on the basis of measuring the time taken by ionized molecules to move through a drift region to a collector electrode, while under the influence of an electric field. Typically there is provided a counter-flowing drift gas. The length of time required for an ion to drift to the collector is a function of the size and mass of the ion, the length of the drift region, the strength of the electric field, the temperature and pressure in the drift region, and the composition of the drift gas.

In one existing design of IMS instruments, the system is operated in two modes: READY and ANALYSIS. In READY mode, the only flow in the IMS detector is a flow of drift gas which sweeps the entire length of the unit. In READY mode, when the IMS may be open to atmospheric pressure, certain calibration measurements may be taken.

In ANALYSIS mode, a sample carrier gas also flows into the IMS detector, and both the drift and sample flows exit the detector, optionally aided by suction (hereafter called exhaust flow) from an exhaust port. The sample carrier gas flow (hereafter called sample flow) transports sample molecules into the IMS where they are ionized. During ANALYSIS mode, the IMS detector is sealed from the atmosphere. Thus, unless the sum of the drift flow and sample flow exactly equals the exhaust flow during the transition from READY to ANALYSIS mode and during ANALYSIS mode, the pressure in the IMS detector may increase or decrease. This, in turn, will disrupt the accuracy of the measurements being made during the ANALYSIS mode since the calibration results established during READY mode operation no longer precisely apply. The difference between the exhaust flow, and the sum of the drift flow and sample flow is called the flow balance. In the past, system control efforts have been directed to holding the flow balance at zero.

Calibration of such a system for purposes of identifying sample molecules by their transit times is established during READY mode by the inclusion of calibration molecules of known mass (hereafter called calibrants) in the drift flow. In the READY mode, the calibrant(s) are ionized after they have traversed the drift region, and travel back through the drift region to a collector electrode while under the influence of an electric field. The time taken by calibrant ions to traverse the drift region and reach the collector is called the calibrant drift time, and is used to calibrate the system.

The calibration is established in READY mode, while the system is open to the atmosphere. As a result, the calibration is only valid in ANALYSIS mode if the IMS maintains a near-constant (i.e. atmospheric) pressure during the ANALYSIS period. If the sum of the drift flow and sample flow do not equal the exhaust flow, the pressure in the IMS may change, because the IMS is a sealed system when in ANALYSIS mode, reducing the validity of the calibration, and the accuracy of the system.

In the past, separate mass flow controllers were used to control the drift flow, sample flow, and exhaust flow in order to maintain the stability of the pressure during ANALYSIS mode. Unfortunately, mass flow controller calibration is prone to drift over time. If one or more of the mass flow controllers drifts over time, the flow balance may change, resulting in an increase or decrease of pressure in the IMS during the ANALYSIS period. In addition, pressure changes during an analysis may result from an initial pressure increase, caused by rapid heating and expansion of trapped gases, when changing from the open READY mode to the closed ANALYSIS mode. These pressure changes and instabilities will render the calibration less valid and reduce system accuracy.

An objective of this invention is, therefore, to maintain pressure in the IMS nearly constant during the transition from READY to ANALYSIS mode and during the ANALYSIS period, in order to preserve the validity of the calibration.

The invention in its general form will first be described, and then its implementation in terms of specific embodiments will be detailed with reference to drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

The invention applies to an ion mobility spectrometer that operates in alternate READY and ANALYSIS modes wherein the pressure of the gas in the drift region may change when switching from READY mode to ANALYSIS mode. More specifically, the invention provides a pressure control means to maintain a near-constant gas pressure in the ion mobility spectrometer's drift region over the transition from READY to ANALYSIS mode, and during the ANALYSIS period.

The objective of pressure stabilization is achieved by replacing a mass flow controller with a variable flow control valve in the flow of the drift flow, sample flow, or exhaust flow. Such a valve is operated in response to a differential pressure sensor which measures the gas pressure in the IMS drift region and functions to maintain a constant pressure state within the IMS over the transition from READY to ANALYSIS mode.

The foregoing summarizes the principal features of the invention and some of its optional aspects. The invention may be further understood by the description of the preferred embodiments, in conjunction with the drawings, which now follow.

DESCRIPTION OF THE PREFERRED EMBODIMENT

Figure 1:
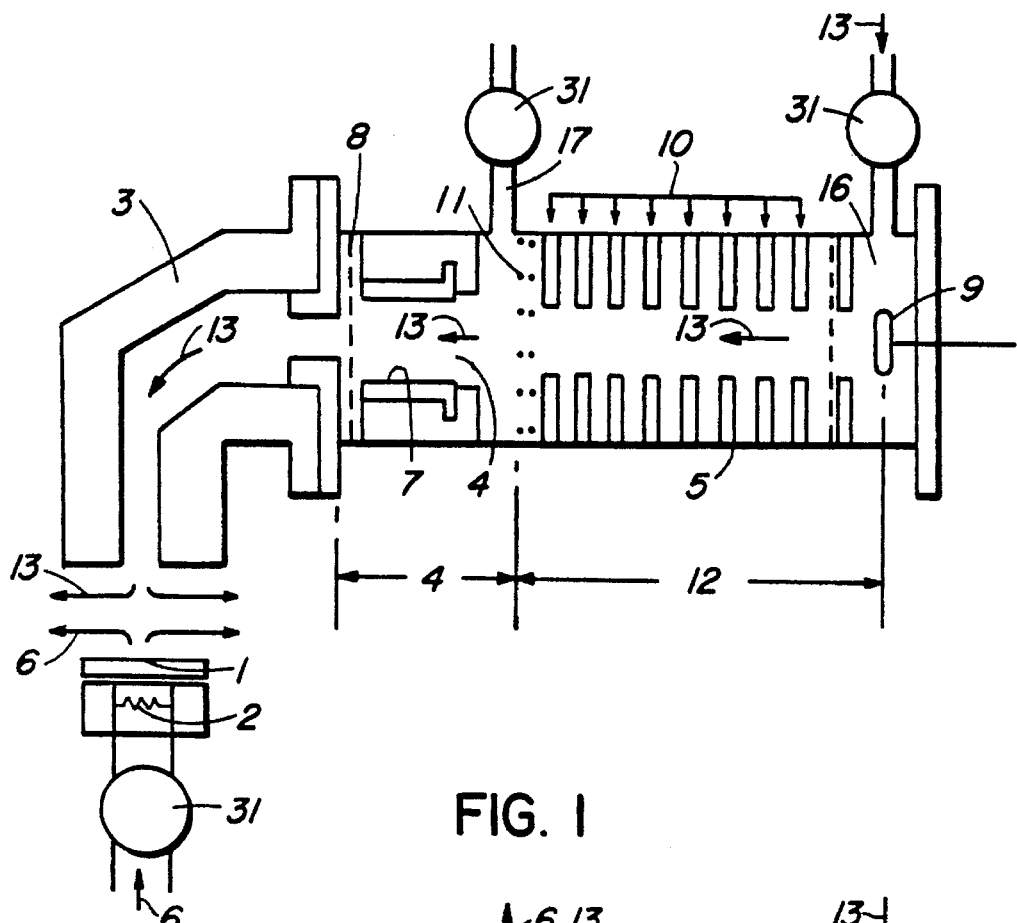
FIG. 1 is a schematic cross-section of the prior art IMS detector, open to the atmosphere in READY mode, before and between analyses. It is during this time that the calibrant ions drift time is measured.
Figure 2:
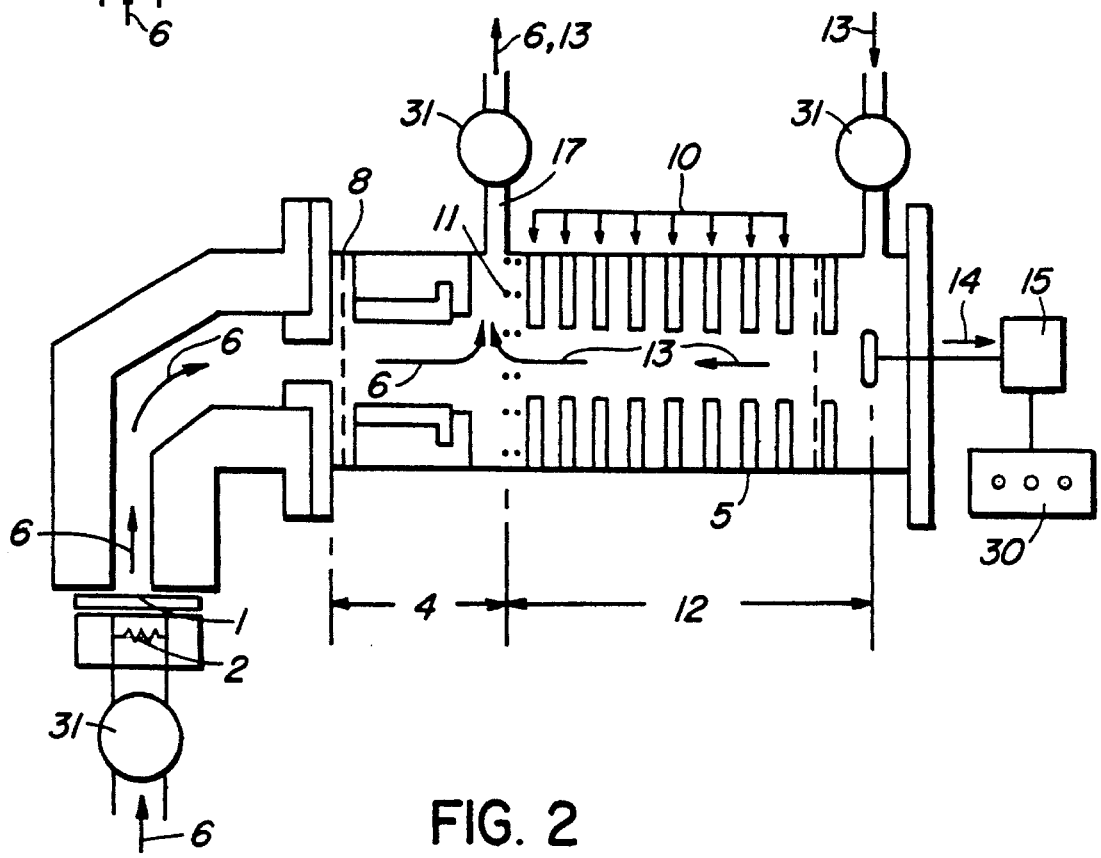
FIG. 2 is a schematic cross-section of instrument gas flows in the ANALYSIS mode of the prior art IMS detector of FIG. 1, operating at atmospheric pressure, during which time the sample is provided and ionized, and the drift times of the resulting sample ions are measured.

Certain IMS systems incorporate internal calibrant features, and rely on a transition from a calibration (or READY) mode to a sample testing (or ANALYSIS) mode. An IMS of this prior art is illustrated in FIGS. 1 and 2. The testing procedure is shown in FIG. 2 wherein vapours from the sample (1) (consisting of particles or other condensed phase are liberated by application of heat from a desorber heater (2). The vapours are carried through a heated sample gas inlet passageway (3) to the ionization/reaction region (4) of the IMS drift tube (5) by a flow of sample carrier gas (6). Alternatively, samples already in the vapour state may be introduced in a similar fashion or by injection through a septum.

Vapours in the ionization/reaction region (4) are ionized by electrons emitted from an electron source such as $^{63}$Ni (7), and by interactions with other vapour molecules present, which may include added reactants. An electric field gradient is established between the repelling ring (8) at the entrance to the drift tube (5) and the collector electrode (9) at the other end of the drift tube through the use of drift rings (10) in the drift region (12). Ions of appropriate polarity move to the electronic gating grid (11), which separates the ionization/reaction region (4) and the drift region (12) of the drift tube (5).

Progress of ions to the drift region is stopped by a small opposite potential at the gating grid (11). This gating grid potential is periodically reversed for short periods of time, typically 200 microseconds, during which interval a packet of ions enters the drift region (12) and moves towards the collector electrode (9) against a counterflow of drift gas (13). During this movement, the different ionic species in the packet separate, with the smaller, lighter ions reaching the collector electrode (9) ahead of larger, heavier ions.

Current at the collector electrode (9), produced by the arrival of such ions is measured, and may be presented as a function time elapsed from the last gating pulse, i.e. as an "analysis window". This transit time is called drift time. Typically up to 30 milliseconds elapse between gating pulses. The collector current signals (14) are amplified and digitized in a processor (15), with multiple scans being combined to form one analysis window, typically consisting of about 20 scans. Several analysis windows are obtained throughout the sample desorption period of typically 5 to 10 seconds and are used to provide an output (30).

The flow of drift gas (13) containing trace amounts of calibrant(s) enters the drift tube (5) at the collector electrode end (16). This flow is maintained in both READY and ANALYSIS modes. The sample carrier gas flow (6) only enters the inlet passageway (3) and drift tube (5) in the ANALYSIS mode. The exhaust (suction) flow through the exhaust port (17) is only activated during the ANALYSIS mode. In the READY mode, the sample carrier gas flow (6) disperses into the air surrounding the desorber (2), and the exhaust port (17) is closed.

In READY mode, the drift gas containing trace amounts of calibrant(s) therefore passes through the drift tube (5). The calibrant molecules in the drift gas are ionized in the ionization/reaction region (4) and repelled towards the gating grid (11), where the gating pulse allows a packet of ions (including the calibrant(s)) to move into the drift region (12) towards the collector electrode (9).

In the READY mode, calibrant ions are regularly pulsed into the drift region (12), and the calibrant ion drift times are measured. This drift time is used to calculate the expected drift times of the various target ions which may be present during a subsequent ANALYSIS mode.

Since the drift tube (5) and inlet (3) are an open system in the READY mode, the pressure within the drift tube during the READY mode is at or nearly at atmospheric.

In the ANALYSIS mode, depicted in FIG. 2, once a sample (1) is placed on the desorber heater (2) at the entrance to the sample gas inlet passageway (3), the system is sealed at such inlet. Sample carrier gas (6) containing the thermally desorbed sample vapours flows into the ionization/reaction region (4) through the sample gas inlet passageway (3) in a direction counter to the prior flow of the drift gas (13). At the same time, the exhaust port (17) is opened, and the suction provided from beyond the exhaust port (17) draws sample carrier gas (6), drift gas (13), and un-ionized sample vapours out by this means.

At this point, the IMS detector is a sealed unit, as shown in FIG. 2. For the pressure in the detector to remain constant, over the transition, it has previously been arranged to provide that the sum of the drift and flow (13) and sample flow (6) must be equal to the exhaust flow through the exhaust port (17). If this is not the case the pressure in the IMS will increase or decrease over the course of the ANALYSIS period. Furthermore, cold air trapped on top of the sample (1), or material introduced by the vapour or liquid sample introduction techniques will expand in the heated inlet (3) and cause an initial rise in pressure. Such pressure instabilities have been measured and can typically be at levels in the range of 0.05 to 0.35 kPa.

Flow stability has in the past been maintained by controlling the drift, sample, and exhaust flows with mass flow controllers (31). The calibration of these controllers (31) tends to drift over time, which may result in a flow imbalance resulting in a change in the pressure inside the IMS drift tube.

Any pressure changes in the drift tube (5) between the READY and ANALYSIS modes cause the drift times of the various ionic species to be different in the ANALYSIS and READY modes. This effect would not be a problem if the drift times of analyte and calibrant ion species were both measured in the ANALYSIS mode, but the competitive nature of the IMS ionization process often results in the calibrant ionization being suppressed by analytes and other materials in the sample, so that calibrant ion drift times can only be reliably measured during the READY mode immediately prior to the analysis. Expected drift times for target ions during the analysis are calculated from the calibrant ion drift time measured in the READY mode.

It has been determined that drift times are particularly sensitive to pressure. The pressure differences and instabilities in the ANALYSIS mode result in inaccuracies, of 20 microseconds or more, in the calculated drift times of the target ions. For comparison, a typical drift tube of 10 cm length and 200 V/cm field provides analyte drift times between 12 and 24 milliseconds if operating at atmospheric pressure. However, for example, the intervals between differing sample species may be on the order of 20 microseconds, necessitating a detection window of 10 microseconds width on either side of the calculated drift time. An inaccuracy in the drift time calculation of 20 microseconds or more due to a pressure instability may therefore result in false positive alarms due to a peak appearing in an incorrect detection window, or in false negative alarms due to a peak not appearing in the correct detection window. Consequently a means to obviate or control this pressure instability is most desirable and is the subject of this invention.

Figure 3:
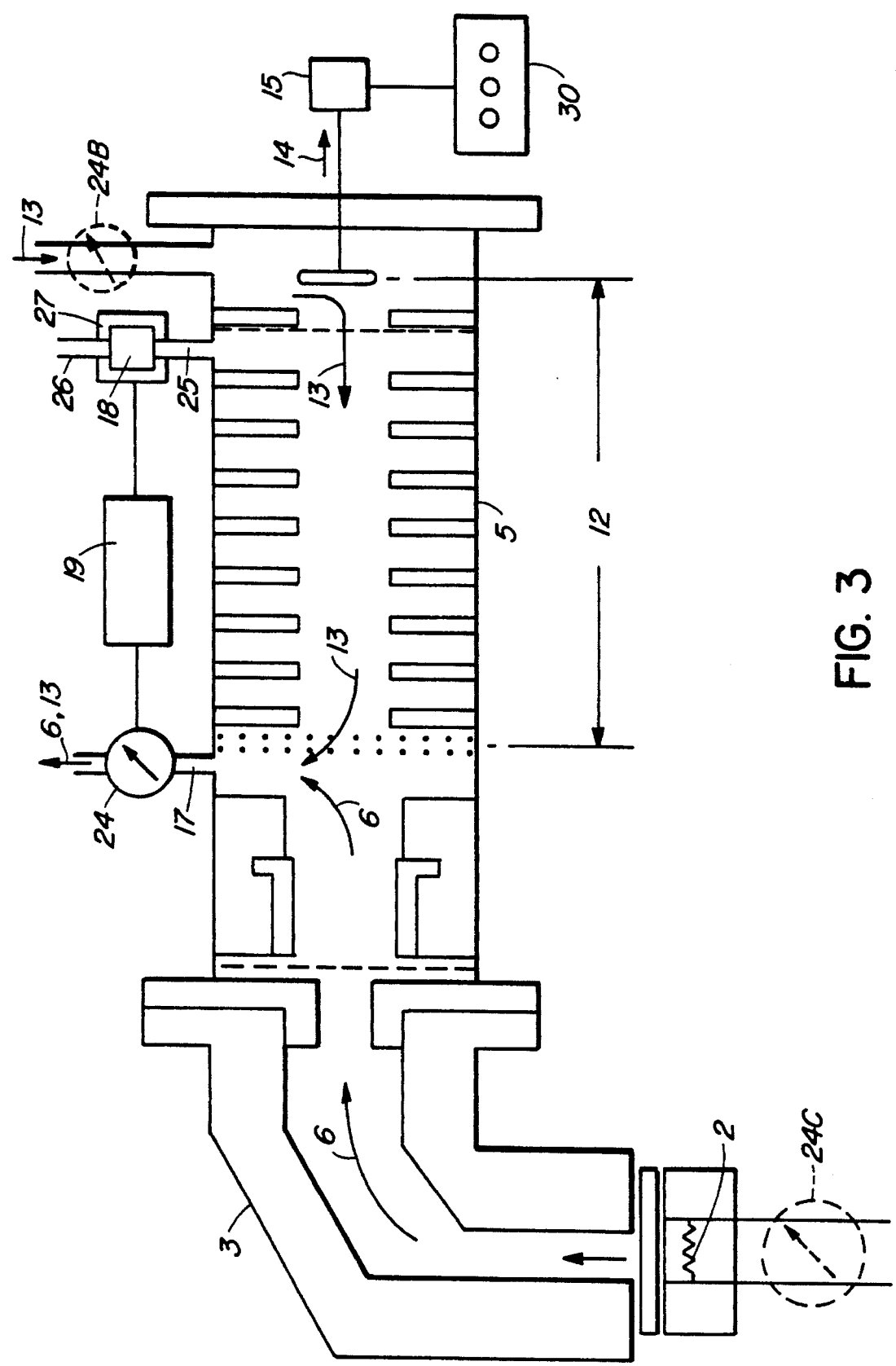
FIG. 3 is a schematic cross-section of an IMS detector operating at atmospheric pressure, and incorporating pressure monitoring and flow control means, showing flows in the ANALYSIS mode.

The present invention, illustrated in FIG. 3, is a means of ensuring that the pressure of gas within the drift region (12) is stable throughout most of the analysis period, and is the same as the pressure in the IMS tube during the READY mode in which the calibrant ion(s) drift time is measured. Alternatively, the system can be used to control the pressure in the IMS drift tube with reference to any other reference pressure. The method involves the use of a pressure transducer (18) and a variable flow control valve (24), and makes the presence of mass flow controllers unnecessary.

The pressure transducer (18) measures the pressure in the drift tube (5) by means of a port (25) connected to the interior of the drift tube (5), and compares that pressure to a reference pressure measured by its second port (26) which is not connected to the drift tube (5). Typically, the reference pressure is atmospheric. If any pressure differential develops between the pressure within the drift tube (5) and the reference pressure, the pressure in the drift tube (5) is rapidly returned to reference pressure by means of a looped control system including a controller (19) (which may include an analogue to digital converter to permit use of a digital type computer to serve as the controller) and a variable flow control valve (24), shown located at the exhaust port (17). Alternately, the reference pressure may be different from atmospheric, including vacuum, in which case the control system maintains a constant pressure difference between the drift tube pressure and the reference pressure.

This flow control valve (24) could easily be positioned to control any one of the exhaust flow (17), sample flow (6), or drift flow (16) ports, and such latter variants are shown in dotted outline on FIG. 3 as valves 24B and 24C.

FIG. 3 illustrates the preferred embodiment of the invention wherein the pressure transducer (18) generates an output voltage proportional to the difference in pressure measured through its two ports (25) and (26). This voltage may be sent to a computer, wherein it may undergo analog-to-digital conversion. After digitization, the computer calculates a control value which, following reverse digital/analog conversion, adjusts the variable flow control valve (24) that controls the volume of the exhaust gas flow (6,13) and thereby the pressure in the drift region.

Where required, the pressure transducer (18) can be provided with a thermostat-controlled heated housing (27) to reduce possible fluctuation of its output signal that might otherwise result from temperature changes.

Figure 4:
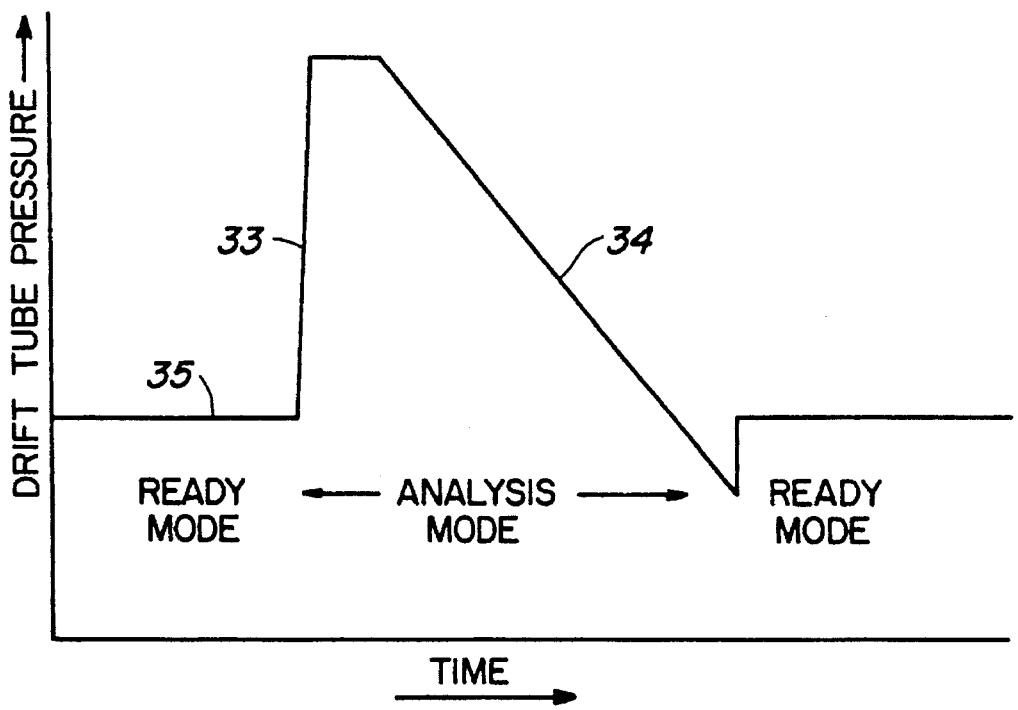
FIG. 4 is a typical plot of pressure versus desorption time within the drift region in the ANALYSIS mode for the prior art IMS detector shown in FIG. 1, operating at atmospheric pressure.

FIG. 4 depicts schematically possible prior art pressure excursions in the IMS over the ANALYSIS period without pressure control. The pressure jump 33 from atmospheric pressure (35) occurring on passage from READY to ANALYSIS mode can occur from the heating of cooler air carrying sample gas into the system. Subsequent pressure behaviour in the ANALYSIS mode is the result of the direction and magnitude of the flow imbalance. The falling pressure curve (34) in FIG. 4 is caused by a relatively large positive flow imbalance, whereas a negative flow imbalance produces a rising pressure curve. In all cases, the pressure reverts to atmospheric in the next READY mode.

Figure 5:
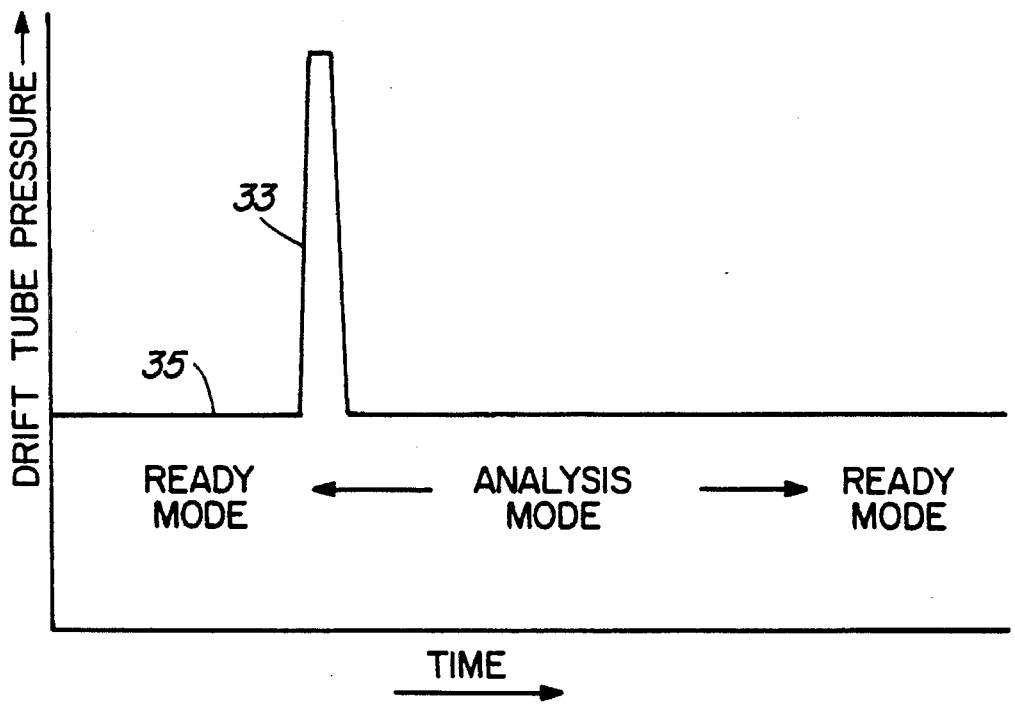
FIG. 5 is a typical plot of pressure versus desorption time within the drift region in the ANALYSIS mode for the IMS detector as shown in FIG. 4.

FIG. 5 depicts schematically possible pressure conditions in the IMS over time when the pressure/flow control system of the invention is employed. The effect of the controller (19) and flow control valve (24) is to restore the original pressure condition in a short interval.

CONCLUSION

The foregoing has constituted a description of specific embodiments showing how the invention may be applied and put into use. These embodiments are only exemplary. The invention in its broadest, and more specific aspects, is further described and defined in the claims which now follow.

These claims, and the language used therein, are to be understood in terms of the variants of the invention which have been described. They are not to be restricted to such variants, but are to be read as covering the full scope of the invention as is implicit within the invention and the disclosure that has been provided herein.

The embodiments of the invention in which an exclusive property are claimed are as follows:

1. An ion mobility spectrometer for analysis of sample gas containing sample molecules comprising:
   (1) a drift tube having a drift gas inlet, a drift region and electronic field generation means for establishing an electrostatic field within the drift region;
   (2) a sample gas inlet;
   (3) an exhaust gas outlet;
   (4) pressure measurement means for detecting the pressure of drift gas in the drift region; and
   (5) flow control means for controlling the flow of gas through any of the drift gas inlet, sample gas inlet, or exhaust outlet in response to said pressure measurements means,
wherein the flow control means adjusts the flow of gas to maintain the pressure in the drift region at a substantially constant value.

2. A spectrometer as in claim 1 wherein the flow control means is positioned to control flow the exhaust gas flow.

3. A spectrometer as in claim 1 wherein the flow control means is positioned to control the drift gas flow.

4. A spectrometer as in claim 1 wherein the flow control means is positioned to control the sample gas flow.

5. A spectrometer as claimed in claims 1, 2, 3, or 4 where said pressure measurement means comprises a differential pressure transducer having two ports, one of which ports is connected to the drift tube assembly, and the other of which ports is connected to a reference pressure.

6. A device as claimed in claim 5 wherein said reference pressure is atmosphere pressure.

7. A device as claimed in claim 5 wherein the flow control means maintains the pressure inside the drift region at a pressure which is constantly different from atmospheric pressure during analysis of sample gas containing sample molecules.

8. A device as claimed in claim 7 wherein said reference pressure is a high vacuum.

9. A device as claimed in claim 1 wherein said flow control means maintains a preset absolute pressure inside the drift region during analysis of samples, independently of the atmospheric pressure.

10. A device as claimed in claims 1, 2, 3 or 4 wherein said pressure measurement means is mounted inside a temperature-controlled housing.

* * * * *